United States Patent [19]

Mori et al.

[11] 4,205,163

[45] May 27, 1980

[54] TYLOSIN DERIVATIVES

[75] Inventors: Shunro Mori; Rokuro Okamoto, both of Fujisawa; Taiji Inui, Chigasaki; Tomio Takeuchi, Tokyo, all of Japan

[73] Assignee: Sanraku-Ocean Co., Ltd., Tokyo, Japan

[21] Appl. No.: 954,055

[22] Filed: Oct. 23, 1978

[30] Foreign Application Priority Data

Nov. 8, 1977 [JP] Japan .................................. 52/134428
Nov. 9, 1977 [JP] Japan .................................. 52/134961

[51] Int. Cl.$^2$ ...................... A61K 31/71; C07H 17/08
[52] U.S. Cl. ................................. 536/17 R; 424/180; 536/9
[58] Field of Search ........................................ 536/9, 17

[56] References Cited

U.S. PATENT DOCUMENTS 4,092,473 5/1978 Okamoto et al. ...................... 536/17

Primary Examiner—Johnnie R. Brown
Attorney, Agent, or Firm—Frank J. Jordan

[57] ABSTRACT

A number of 4"-acyl derivatives of tylosin and acetyltylosin which are prepared by first protectively acylating at the 2'-hydroxyl group of tylosin or acetyltylosin, secondly at the 4'''-hydroxyl group thereof, thirdly at the 4"-hydroxyl group thereof and finally deacylating the 2'- and 4'''-acyl groups to produce new 4"-acyl derivatives of tylosin or acetyltylosin which effect high blood level compared to those tylosin derivatives heretofore are disclosed.

50 Claims, 5 Drawing Figures

TYLOSIN DERIVATIVES

DETAILED EXPLANATION OF THE INVENTION

The present invention relates to new derivatives of the antibiotic tylosin. And more particularly, it relates to new acyl derivatives of tylosin of the following formula I:

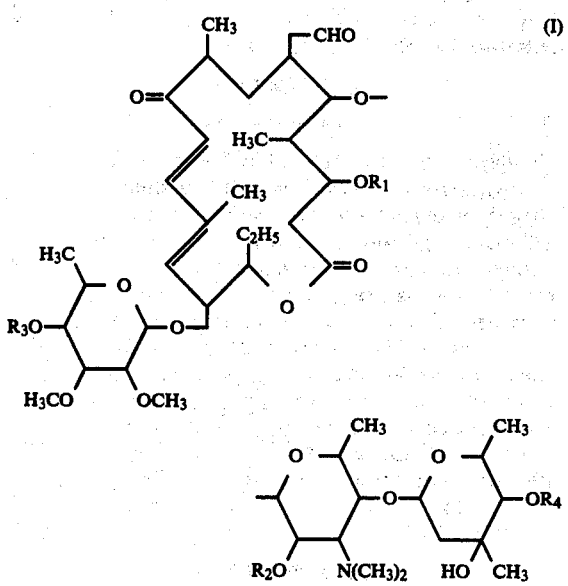

wherein $R_1$ represents hydrogen or acetyl $R_2$ represents hydrogen, acetyl, propionyl or chlorinated acetyl, $R_3$ represents hydrogen, chlorinated acetyl, carboethoxy or phenoxyacetyl, and $R_4$ represents a hydrogen or a

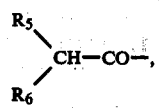

wherein $R_5$ represents hydrogen, methyl, ethyl, hydroxyl or acetoxy, and $R_6$ represents an alkyl having 3 to 8 carbon (when the number of the carbons is 3, $R_5$ being a group other than hydrogen), phenyl, naphthyl, benzyl, cyclohexylmethyl, thienyl, pyridyl, N-acetylanilino, imidazolylmethyl, phenylthio, benzylthio, phenylthiomethyl, cyclohexylthio, pyridylthio, benzenesulfonyl, phenoxy, naphthoxy or phenoxymethyl, with the proviso that when $R_4$ represents hydrogen, $R_2$ and $R_3$ each represent a group other than hydrogen, and when $R_4$ represents a group other than hydrogen, $R_2$ and $R_3$ each represent a hydrogen.

Among acyl derivatives of tylosin prepared by chemical synthesis, acetyltylosin and propionyltylosin are known which have been described in Japan Kokoku Showa 36-22649 and Antibiotics and Chemotherapy 11(5), 328–334 (1961). There has been described in the above references acetyltylosin (m.p. 124°–127° C., $\lambda_{max}^{MeOH}=282$ nm, $E_{1cm}^{1\%}=205$ and $[\alpha]_D^{25}=58.7°$) that was obtained by dissolving tylosin in acetone containing potassium bicarbonate, adding acetyl chloride to the solution while stirring and reacting it for 3 hours at room temperature. They also described propionyltylosin (m.p. 101°–111° C., $\lambda_{max}^{MeOH}=282$ nm and $E_{1cm}^{1\%}=204$) that was obtained by reacting tylosin with propionic acid in the presence of N,N'-dicyclohexyl carbodiimide in dichloromethane for 20 hours. However, no position of the hydroxyl group in the molecule that is acylated is given. The present inventors prepared the acetyltylosin and propionyltylosin of the above-mentioned references according to the method described in them. The physico-chemical properties of the obtained compounds were compared with those of 2'-acetyltylosin and 2'-propionyltylosin produced in Experiments 1 and 2 in the present specification. The results showed that the compounds described in the references mentioned above were tylosin derivatives which were acylated only at the hydroxyl group of 2'-position.

There are provided by the present invention acyl derivatives of tylosin and 3-acetyl tylosin that are selectively acylated at the 4"-, or the 2'- and 4'''-positions of the molecule, respectively. All the derivatives are new compounds that are undoubtedly distinguished from the known derivatives.

The present inventors discovered a method by which tylosin is selectively acylated at the specific hydroxyl group of the molecule, while they were engaged in the study on acylation of macrolide antibiotic tylosin. On the discovery they reported new acyl derivatives of tylosin as mentioned below. That is, they looked for a microorganism that can acylate 3- and 4"-hydroxyl groups of tylosin to clarify biochemical acylation of 3- and 4"-hydroxyl groups of the antibiotic, and found that a microorganism belonging to the genus Streptomyces can selectively acylate 3- and/or 4"-hydroxyl group of tylosin, angoramycin or spiramycin. According to this discovery there was provided a method for producing new antibiotics that are acylated specifically at 3- and/or 4"-position of tylosin-group compounds and other macrolide antibiotics. As described in Belgium Pat. No. 849847, the acyl derivatives of tylosin show similar antimicrobial activity on gram-positive bacteria to tylosin. In particular, the derivatives acylated at the 4"-hydroxyl group have remarkable antimicrobial activity on the resistant strains to various drugs. Also these compounds produced a mugh higher blood level than tylosin when they were administered orally to mice. Therefore it has been shown that the acyl derivatives are effective and useful chemotherapeutic agents against gram-positive bacterial infections when given orally.

The present inventors, based on the above-mentioned discovery, have studied on selective acylation of 4"-hydroxyl group of tylosin with various acyl groups in order to find new acyl derivatives that have much more advantages.

The above-mentioned biochemical acylation is excellent in specificity of the acylated position of the molecule and also in the production yield, but the kind of acyl group to be introduced is limited. To conquer the defect acylation by chemical synthesis has been studied.

It has been found by the present invention that 4"-hydroxyl group of tylosin can be selectively acylated with any desired acyl group based on the difference in reactivity of 3-, 2'-, 4"- and 4'''-hydroxyl group which can be acylated.

One aspect of the present invention therefore comprises new acyl derivatives and a process for producing them. Among the new compounds, the derivatives that are acylated at the 4"-hydroxyl group show the same minimum inhibitory concentration values (MIC) as tylosin, and particularly, they have higher antimicrobial activity on drug-resistant microorganisms. Furthermore, they are absorbed excellently within the digestive system when they are given orally.

Another aspect of the present invention therefore comprises useful compounds as effective chemotherapeutic agents having the excellent properties mentioned above. The derivatives that are acylated at the 2'- and 4'''-hydroxyl groups have similar antimicrobial activity to tylosin and are useful as antimicrobial agents by themselves. But they are particularly advantageous when they are used as the intermediate for producing the above-mentioned derivatives acylated at the 4"-hydroxyl group.

The chemical synthesis of the compound according to the present invention is as follows:

Chemical synthesis

The starting material which may be employed in the chemical synthesis of the present invention is tylosin or 3-acetyltylosin and salt thereof. The 3-acetyltylosin is a new compound that was found to produce a good yield by the present inventors. Belgium Patent 849847 discloses the process thereof.

Extensive studies on the difference in reactivity of 4"- and 4'''-hydroxyl group of tylosin and of 3-acetyltylosin acylated at the 2'-hydroxyl group led the present inventors to the discovery that the hydroxyl group at the 4'''-position may be selectively acylated under specific reaction conditions.

That is, when the tylosin derivative acylated at the 4"-hydroxyl group is produced, at first the 2'-hydroxyl group should be protected by the known acylation method. And then the 4'''-hydroxyl group should also be protected selectively by acylation with a specific acyl group that can be easily removed by hydrolysis under specific conditions found by the present inventors.

The tylosin or 3-acetyltylosin that is protected at the 2'- and 4'''-hydroxyl group is treated with an acylating agent to acylate the 4"-hydroxyl group. The aimed tylosin derivative that is acylated at the 4"-hydroxyl group with the desired acyl group is produced by removing the protective groups at the 2'- and 4'''-position of the reaction product by selective hydrolysis.

Acylation of hydroxyl group at 2'-position

At the first step of the process according to the present invention, 2'-acyltylosin or 3-acetyl-2'-acyltylosin is produced, that is, tylosin or 3-acetyltylosin that is selectively protected at the 2'-hydroxyl group with an acyl group. This selective acylation of the 2'-hydroxyl group may be carried out by the conventional method that is known as the acylation procedure of common macrolide antibiotics. Acyl groups which may be employed for the substitution are, for example, a lower alkanoyl group such as acetyl, propionyl or butyryl group, a lower haloalkanoyl group such as monochloroacetyl, trichloroacetyl, monobromoacetyl or trifluoroacetyl group, a lower alkoxycarbonyl group such as methoxycarbonyl or ethoxycarbonyl group, and an aryloxyalkanoyl group such as phenoxyacetyl group.

As the acylating agent, carboxylic acids, acid halides and acid anhydrides corresponding to the acyl groups mentioned above are suitable for the present method. Acetyl chloride or acetic anhydride is advantageous in the yield and specificity of reaction.

If carboxylic acid, acid halide or acid anhydride is employed as the acylating agent, 2'-acyltylosin or 3-acetyl-2'-acyltylosin that is selectively protected at the 2'-hydroxyl group with an acyl group is obtained as shown in the following experiment.

EXPERIMENT 1

2'-Acetyltylosin

Tylosin (1 g) was dissolved in 7 ml of acetone with 1 g of potassium bicarbonate added to the solution. A solution prepared by dissolving 0.4 g of acetyl chloride in 0.3 ml of acetone was added dropwise while stirring at room temperature. The reaction mixture was, after a further 5 hours-stirring at room temperature, poured in ice water. The mixture was extracted with 10 ml of benzene twice. The benzene layer was washed with saturated aqueous solutions of sodium bicarbonate and sodium chloride successively and then dried with anhydrous sodium sulfate. White powder was obtained by evaporating benzene under reduced pressure. Recrystallization from toluene provided 1 g of pure 2'-acetyltylosin (m.p. 123°–127° C. and $[\alpha]_D^{22}$ in MeOH= −74.8°).

EXPERIMENT 2

2'-Propionyltylosin

Tylosin (1 g) and 0.22 g of N,N'-dichlorohexyl carbodiimide were dissolved in 20 ml of dichloromethane. Propionic acid (0.16 g) was added while stirring at room temperature and allowed to stand at the same temperature overnight. The resulted precipitate was removed by filtration and the filtrate was treated in the same manner as described in Experiment 1. Recrystallization from acetone provided 0.7 g of pure 2'-propionyltylosin (m.p. 115.5°–118.5 ° C. and $[\alpha]_D^{22}$ in MeOH= −56.8°).

EXPERIMENT 3

3,2'-Diacetyltylosin

3-Acetyltylosin (1 g) was added to 5 ml of acetic anhydride and stirred at room temperature. Immediately after the mixture became a homogenous solution, the reaction mixture was poured in 45 ml of ice water to stop the reaction. The aqueous solution was extracted with benzene after the pH was adjusted to 7.5–8.0, and then treated in the same manner as described in Experiment 1 to provide a white powder Recrystallization from carbon tetrachloride provided 1 g of pure 3,2'-diacetyltylosin (m.p. 117°–119° C. and $[\alpha]_D^{22}$ in MeOH= −41.4°).

Acylation of the 4'''-hydroxyl group of the compound that is acylated at the 2'-hydroxyl group The compound acylated at the 2'-hydroxyl group obtained by the process mentioned above is treated with an appropriate acylating agent in the presence of basic reagent such as pyridine in a solvent such as methylene chloride to acylate the 4'''-hydroxyl group selectively.

Thus there is provided the aimed product of the present invention, the compound that is acylated at the 2'- and 4'''-hydroxyl groups of the following formula II:

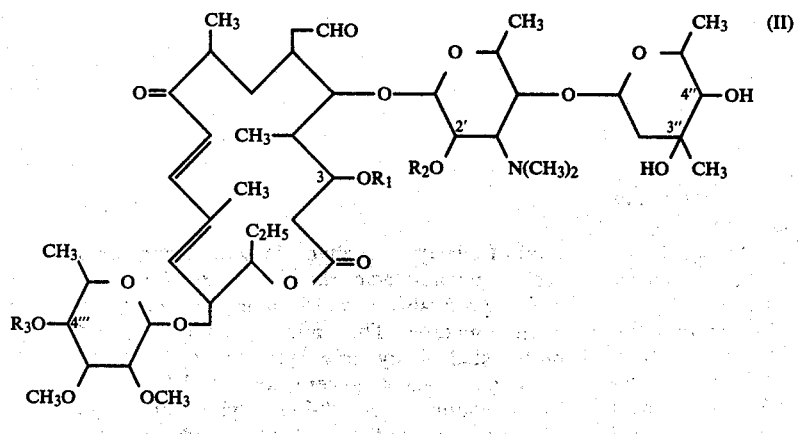

wherein $R_1$ represents hydrogen or acetyl, $R_2$ represents acetyl, propionyl or chlorinated acetyl, and $R_3$ represents chlorinated acetyl, carboethoxy or phenoxyacetyl.

As the acyl group employed for the protection of the 4'''-hydroxyl group, those groups should be selected that are more easily removed than the acyl group at the 4''-position when the protecting groups at 2'- and 4'''-position are removed by hydrolysis. Such acyl groups are for example a lower haloalkanoyl group such as monochloroacetyl, trichloroacetyl, monobromoacetyl or trifluoroacetyl group, a lower alkoxycarbonyl group such as methoxycarbonyl or ethoxycarbonyl, and an aryloxyalkanoyl group such as phenoxyacetyl group.

Reactive derivatives such as carboxylic acids, acid halides or acid anhydrides corresponding to the above-mentioned acyl groups may be employed as the acylating agent. Advantageously, monochloroacetyl chloride and trichloroacetyl chloride are used because of the stability and selectivity in acylation and deacylation.

The following experiments show the acylation of 4'''-hydroxyl group with monochloroacetyl chloride.

EXPERIMENT 4

2'-Acetyl-4'''-monochloroacetyltylosin

2'-Acetyltylosin (1 g) was dissolved in 20 ml of methylene chloride. After 0.16 g of pyridine was added to the solution, the mixture was cooled at $-15°$ - $-10°$ C. To the reaction mixture was added 0.28 g of monochloroacetyl chloride while vigorously stirring. The reaction was continued for 5 minutes. The reaction mixture was poured in water-saturated toluene. The toluene solution was washed with saturated aqueous solutions of sodium bicarbonate and sodium chloride successively. The toluene layer, after drying, was removed by evaporation under reduced pressure to provide 1.08 g of white powder. The powder was subjected to column chromatography in a silica gel column (1.8 cm in outer diameter and 25 cm in length). The eluate with benzene-acetone (0–20% V/V acetone) was evaporated to dryness to provide 0.62 g of 2'-acetyl-4'''-monochloroacetyltylosin in white powder (m.p. 127°–132° C. and $[\alpha]_D^{22}$ in MeOH = $-25.6°$).

EXPERIMENT 5

3,2'-Diacetyl-4'''-monochloroacetyltylosin 3,2'-Diacetyltylosin (1 g), monochloroacetyl chloride (0.27 g) and pyridine (0.15 g) were treated and the product was purified in the same manner as described in Experiment 4 to provide 0.60 g of 3,2'-diacetyl-4'''-monochloroacetyltylosin (m.p. 111°–113° C. and $[\alpha]_D^{22}$ in MeOH = $-35.8°$).

Another aimed compound in the present invention, that is, tylosin or 3-acetyltylosin that is acylated at the 4''-hydroxyl group is produced as follows:

The tylosin or 3-acetyltylosin that is acylated at the 2'- and 4'''-hydroxyl groups of the formula II is treated with the compound of the following formula III:

wherein

X represents halogen or pivaloyloxy, and $R_5$ and $R_6$ represent the same meaning as previously defined, to obtain the compound of the following formula IV:

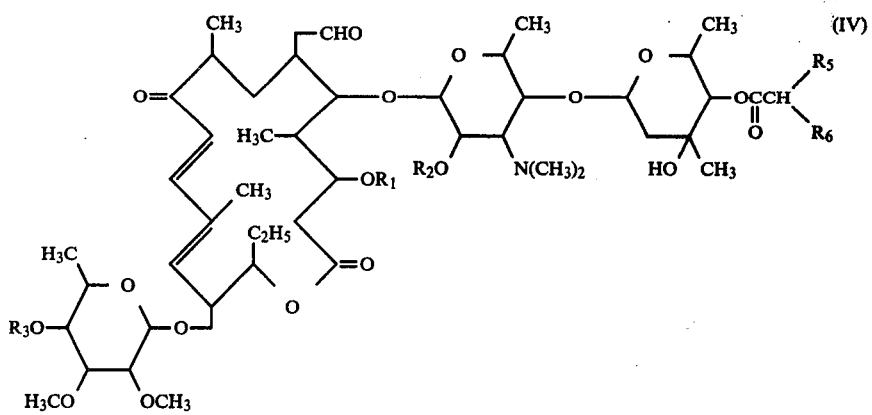

(IV)

wherein $R_1$, $R_2$, $R_3$, $R_5$ and $R_6$ represent the same meaning as previously defined. The compound thus obtained is subjected to hydrolysis or alcoholysis to deacylate the $R_2$ and $R_3$ selectively to produce the aimed compound of the present invention.

The 4″-hydroxyl group of the tylosin derivative acylated at the 2′- and 4‴-hydroxyl groups is generally acylated easier than the 3-hydroxyl group in the reaction of the compound of the general formula II with that of the general formula III. When the 4″-hydroxyl group is acylated according to the process of the present invention, a slight amount of 3,4″-diacyl derivative is sometimes formed as a by-product depending on the acylating agent employed.

On the other hand, 3-acetyltylosin acylated at the 2′- and 4‴-positions is already acylated at the 3-position. Therefore it provides the aimed 3-acetyl-4″-acyl derivative in high yield because the 4″-hydroxyl group is selectively acylated without formation of the by-product.

Corresponding acid halides, acid anhydrides or mixed acid anhydrides with appropriate acids such as pivaloic acid are suitably used as the reactive derivatives of carboxylic acid compound in the process of the present invention.

When the acid halides of carboxylic acid of the above-mentioned general formula III or mixed acid anhydrides are employed as the acylating agent, the reaction is accomplished in the presence of a basic reagent. Preferred basic reagents are pyridine, picoline, piperidine and triethylamine. A comparably weak base such as pyridine is more preferred.

In general the reaction mentioned above is carried out in an inert organic solvent such as benzene, toluene, chloroform, methylene chloride, tetrahydrofuran or a mixture thereof. The basic reagent itself may be used as the solvent for the reaction.

The temperature for the reaction may be in a range between −20° and 50° C., but a higher reaction allows the formation of a by-product. Generally the preferred reaction temperature is between −10° C. and room temperature.

When acid halide is employed as the acylating agent in the above-mentioned reaction, it is generally used in a 3 to 20 moles per one mole of the starting material of formula II. The amount of basic reagent depends on the kind of acylating agent employed. An acylating agent of low reactivity requires a larger amount. In general, a 4 to 10 moles per one mole of the starting material is preferred. When a free carboxylic acid is used in the form of mixed acid anhydride with an appropriate acid such as pivaloic acid, the amount employed is 4 to 20 moles, preferably 6 to 15 moles per one mole of the starting material. The amount of basic reagent depends on the kind of acylating agent employed. As examples of acylating agent (general formula III) employed for the acylation of the 4″-hydroxyl group of the compound of formula II the following carboxylic acid compounds shown in Table 1 are mentioned.

Table 1

A compound of formula III: $\begin{array}{c} R_5 \\ \diagdown \\ CHCOX \\ \diagup \\ R_6 \end{array}$ (X represents a halogen atom or a pivaloyloxy group.)

| $R_5$ | $R_6$ |
|---|---|
| CH₃CH₂— | CH₃CH₂— |
| CH₃— | CH₃(CH₂)₂— |
| H | CH₃(CH₂)₃— |
| H | CH₃CH(CH₃)CH₂— |
| H | CH₃(CH₂)₅— |
| H | CH₃(CH₂)₇— |
| H | O₂N—C₆H₄— |
| CH₃— | C₆H₅— |
| CH₃CH₂— | C₆H₅— |
| HO— | C₆H₅— |

Table 1-continued
A compound of formula III: $\underset{R_6}{\overset{R_5}{>}}$CHCOX
(X represents a halogen atom or a pivaloyloxy group.)
| R5 | R6 |
|---|---|
| CH3COO— | 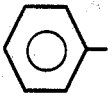 |
| CH3COO— | 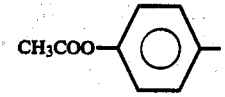 |
| H | 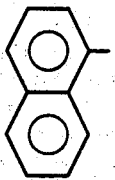 |
| H | 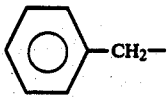 |
| HO— | 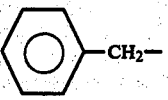 |
| CH3COO— | 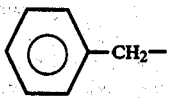 |
| CH3COO— | 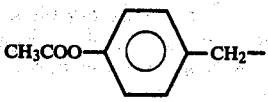 |
| H | 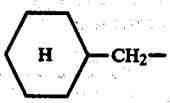 |
| H | 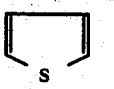 |
| H | 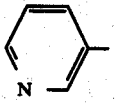 |
| H | 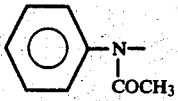 |
| H | 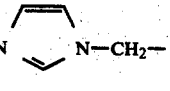 |
| H |  |
| H | 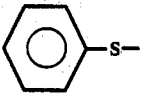 |
| H | 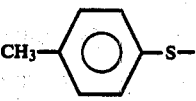 |
| H | 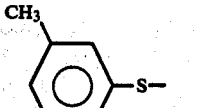 |
| H |  |
| H | 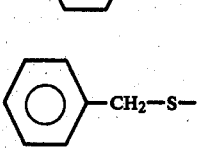 |
| H |  |
| H | 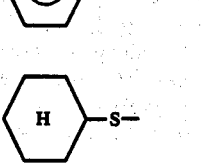 |
| H |  |
| H |  |
| H | 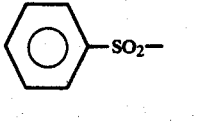 |
| H | 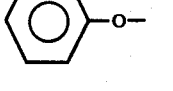 |
| H | 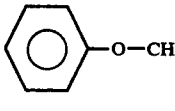 |
| CH3— |  |

Table 1-continued

A compound of formula III: 
$$\begin{array}{c} R_5 \\ \diagdown \\ CHCOX \\ \diagup \\ R_6 \end{array}$$

(X represents a halogen atom or a pivaloyloxy group.)

| $R_5$ | $R_6$ |
|---|---|
| H |  |

The compound of general formula IV obtained by the reaction mentioned above is isolated from the reaction mixture as follows:

A solvent such as benzene, toluene or ethyl acetate is added to the reaction mixture. The solution is washed with saturated aqueous solutions of sodium bicarbonate and of sodium chloride successively, and if necessary, with a buffer solution, pH 5–6, and then the solvent is removed by evaporation under reduced pressure. In some case it is further purified by column chromatography on alumina or silica gel, or counter current extraction, which is known per se. Thus the aimed product, tylosin that is acylated at the 2′-, 4″- and 4‴-hydroxyl groups or 3-acetyltylosin that is acylated at the 2′-, 4″- and 4‴-hydroxyl groups is obtained.

Partial hydrolysis of the compound of formula IV obtained by the above-mentioned procedure is carried out as follows:

The compound is dissolved in lower alcohol such as methanol or ethanol, or in an aqueous organic solvent. In some case a trace of ammonia or alkali is added to the aqueous organic solvent. The solution is treated at a temperature in a range between room temperature and the boiling point of the solvent for 5 hours to 3 days. By the treatment, only the acyl groups at the 2′- and 4‴-position are selectively hydrolyzed and the aimed compound of the present invention, 4″-acyl derivative is obtained.

As the preferred aqueous organic solvent, a 5–20% (V/V) water-containing solvent such as methanol, ethanol, acetone or tetrahydrofuran may be used. Preferably sodium carbonate or sodium bicarbonate is employed as examples of alkali mentioned above.

The 4″-acyl derivative thus produced in the reaction mixture may be recovered by adding benzene, toluene or ethyl acetate after evaporating most of the solvent in the reaction mixture, washing the organic layer with saturated aqueous solution of sodium bicarbonate and then evaporating the solvent under reduced pressure. If necessary, further purification by other techniques such as column chromatography may be employed. Thus a new compound 4″-acyltylosin or 3-acetyl-4″-acyltylosin having each an acyl group corresponding to the acylating agent employed is obtained in a pure preparation, which is the aimed compound of the present invention shown by formula I.

Suitable salts of the new tylosin derivatives of general formula I according to the present invention are produced with pharmaceutically allowable inorganic or organic acids. The salts employable for the purpose are those that may be used in pharmaceutical chemistry, particularly in antibiotic chemistry. Suitable examples of such acids are organic acids such as tartaric acid, acetic acid, propionic acid, citric acid, or succinic acid, and inorganic acids such as hydrochloric acid or phosphoric acid.

For example, the tylosin derivative of formula I and an equivalent amount of such acid is each independently dissolved in ethylether, acetone or a mixture thereof. Both the solutions are mixed, if necessary under cooled conditions, to form a salt. The desired salt is separated, if necessary after concentration and cooling, by filtration in a form of white (crystalline) powder. The obtained salts are more soluble in water than a free compound and superior as a drug formulation.

Accordingly, the present invention provides new compounds, 2′,4‴-diacyltylosin, 3-acetyl-2′,4‴-acyltylosin, 4″-acyltylosin and 3-acetyl-4″-acyltylosin derivatives of general formula I, and salts thereof obtained from tylosin or 3-acetyltylosin as the starting material by a process consisting of the ingenious combination of various reactions which were discovered by the present inventors.

Tab. 2 shows the new acyl derivatives of tylosin according to the present invention.

Table 2

| Compound No. | |
|---|---|
| 1 | 2′-acetyl-4‴-monochloracetyltylosin |
| 2 | 2′-acetyl-4‴-trichloroacetyltylosin |
| 3 | 3,2′-diacetyl-4‴-monochloroacetyltylosin |
| 4 | 3,2′-diacetyl-4‴-trichloroacetyltylosin |
| 5 | 2′-acetyl-4‴-phenoxyacetyltylosin |
| 6 | 3,2′-diacetyl-4‴-carboethoxytylosin |
| 7 | 4″-n-caproyl(or n-hexanoyl)tylosin |
| 8 | 3-acetyl-4″-n-caproyl(or n-hexanoyl)tylosin |
| 9 | 4″-n-caprylyl(or n-octanoyl)tylosin |
| 10 | 4″-n-capryl(or n-decanoyl)tylosin |
| 11 | 4″-iso-caproyl(or iso-hexanoyl)tylosin |
| 12 | 4″-α-methyl-n-valeryltylosin |
| 13 | 3-acetyl-4″-α-ethyl-n-butyryltylosin |
| 14 | 4″-(4-nitrophenyl)acetyltylosin |
| 15 | 3-acetyl-4″-α-phenylpropionyltylosin |
| 16 | 4″-α-phenyl-n-butyryltylosin |
| 17 | 3-acetyl-4″-D-(α-hydroxyphenylacetyl)tylosin |
| 18 | 3-acetyl-4″-L-(α-hydroxyphenylacetyl)tylosin |
| 19 | 3-acetyl-4″-D-(α-acetoxyphenylacetyl)tylosin |
| 20 | 3-acetyl-4″-L-(α-acetoxyphenylacetyl)tylosin |
| 21 | 3-acetyl-4″-[α-acetoxy-(4-acetoxyphenyl)acetyl]tylosin |
| 22 | 4″-α-naphthylacetyltylosin |

Table 2-continued

| Compound No. | |
|---|---|
| 23 | 3-acetyl-4''-α-naphthylacetyltylosin |
| 24 | 4''-β-phenylpropionyltylosin |
| 25 | 3-acetyl-4''-β-phenylpropionyltylosin |
| 26 | 3-acetyl-4''-L-[(α-hydroxy-β-phenyl)propionyl]tylosin |
| 27 | 3-acetyl-4''-L-[(α-acetoxy-β-phenyl)propionyl]tylosin |
| 28 | 3-acetyl-4''-[α-acetoxy-β-(4-acetoxyphenyl)propionyl]tylosin |
| 29 | 4''-β-cyclohexylpropionyl tylosin |
| 30 | 4''-thienylacetyltylosin |
| 31 | 3-acetyl-4''-(3-pyridyl)acetyltylosin |
| 32 | 3-acetyl-4''-(N-acetylanilino)acetyltylosin |
| 33 | 3-acetyl-4''-(1-imidazolyl)propionyltylosin |
| 34 | 4''-phenylthioacetyltylosin |
| 35 | 4''-(4-methylphenyl)thioacetyltylosin |
| 36 | 4''-(3-methylphenyl)thioacetyltylosin |
| 37 | 4''-(4-chlorophenyl)thioacetyltylosin |
| 38 | 3-acetyl-4''-benzylthioacetyltylosin |
| 39 | 4''-β-phenylthiopropionyltylosin |
| 40 | 4''-cyclohexylthioacetyltylosin |
| 41 | 4''-(4-pyridyl)thioacetyltylosin |
| 42 | 3-acetyl-4''-(4-pyridyl)thioacetyltylosin |
| 43 | 4''-benzenesulfonylacetyltylosin |
| 44 | 4''-phenoxyacetyltylosin |
| 45 | 3-acetyl-4''-phenoxyacetyltylosin |
| 46 | 4''-α-phenoxypropionyltylosin |
| 47 | 4''-β-napthoxyacetyltylosin |

Physico-chemical properties and structure

All the compounds according to the present invention are white powder or crystalline white or yellowish powder. They are soluble in methanol, ethanol, acetone, diethylether, ethylacetate, benzene, toluene and dimethyl sulfoxide, and hardly soluble in water, n-hexane and petroleum ether.

Elementary analysis, melting point, specific rotation, ultraviolet absorption spectrum (in methanol solution), infrared absorption spectrum (in KBr tablet) and nuclear magnetic resonance spectrum (60 MHz, heavy chloroform) were measured on the compounds according to the present invention as shown in Tab. 3 and FIG. 1-5.

The ultraviolet absorption spectra in the methanol solution and the infrared absorption spectra in the KBr tablet of these compounds are slightly different from each other depending on the substituted acyl group and position. However, they show a similar pattern to that of tylosin. In particular, these compounds have the same ultraviolet absorption maxima at about 281-284 nm as tylosin, which means that there is no change in the ketone and double bond structure of the macrolide ring.

The free compounds show positive in Molisch and conc. $H_2SO_4$ reactions, and negative in ninhydrin, biuret and Millon reactions.

All other compounds according to the present invention were subjected to the same analyses. The results obtained support the structures described in this specification.

Table 3

| analysis | compounds No. | | | | |
|---|---|---|---|---|---|
| | 1 | 2 | 3 | 4 | 5 |
| (1) Elementary analysis (calculated value) | C:58.24(58.04) H: 7.57( 7.79) N: 1.39( 1.35) | C:54.21(54.42) H: 7.43( 7.12) N: 1.31( 1.27) | C:58.38(58.01) H: 7.90( 7.68) N: 1.25( 1.30) | C:54.37(54.52) H: 7.49( 7.04) N: 1.28( 1.22) | C:61.63(61.58) H: 7.60( 7.84) N: 1.31( 1.28) |
| (2) Molecular weight | 1,035 | 1,104 | 1,077 | 1,146 | 1,092 |
| (3) Melting point (°C.) | 127–132 | 129–132 | 111–113 | 116–120 | 109–115 |
| (4) Specific rotation $[\alpha]_D^{22}$ C = 0.5% methanol solution | −25.6° | −46.4° | −35.8° | −20.0° | −54.0° |
| (5) Ultraviolet absorption spectrum $E_{1cm}^{1\%}$ | $\lambda_{max}^{MeOH}$ 284 nm 165 | $\lambda_{max}^{MeOH}$ 283 nm 198 | $\lambda_{max}^{MeOH}$ 283 nm 204 | $\lambda_{max}^{MeOH}$ 282 nm 191 | $\lambda_{max}^{MeOH}$ 281 nm (277–284 flat) 192 |

| analysis | compounds No. | | | | |
|---|---|---|---|---|---|
| | 6 | 7 | 8 | 9 | 10 |
| (1) Elementary analysis (calculated value) | C:59.52(59.37) H: 8.01( 7.99) N: 1.27( 1.31) | C:61.80(61.58) H: 8.93( 8.65) N: 1.41( 1.38) | C:61.53(61.40) H: 8.65( 8.49) N: 1.30( 1.33) | C:62.33(62.23) H: 8.92( 8.80) N: 1.40( 1.34) | C:62.54(62.84) H: 8.67( 8.95) N: 1.25( 1.31) |
| (2) Molecular weight | 1,072 | 1,014 | 1,056 | 1,042 | 1,070 |
| (3) Melting point (°C.) | 104–110 | 105–109 | 98–103 | 90–94 | 85–90 |
| (4) Specific rotation $[\alpha]_D^{22}$ C = 0.5% methanol solution | −38.2° | −59.0° | −32.4° | −48.8° | −68.6° |
| (5) Ultraviolet absorption spectrum | $\lambda_{max}^{MeOH}$ 283 nm 193 | $\lambda_{max}^{MeOH}$ 283 nm 206 | $\lambda_{max}^{MeOH}$ 281.5 nm 214 | $\lambda_{max}^{MeOH}$ 283 nm 205 | $\lambda_{max}^{MeOH}$ 283 nm 184 |

Table 3-continued $E_{1cm}^{1\%}$

| analysis | compounds No. 11 | 12 | 13 | 14 | 15 |
|---|---|---|---|---|---|
| (1) Elementary analysis (calculated value) | C:61.75(61.58) H: 8.80( 8.65) N: 1.49( 1.38) | C:61.66(61.58) H: 8.78( 8.65) N: 1.42( 1.38) | C:61.55(61.40) H: 8.90( 8.49) N: 1.43( 1.33) | C:60.38(60.10) H: 7.45( 7.66) N: 2.61( 2.59) | C:63.05(62.79) H: 8.54( 8.04) N: 1.20( 1.28) |
| (2) Molecular weight | 1,014 | 1,014 | 1,056 | 1,079 | 1,090 |
| (3) Melting point (°C.) | 209–214 | 100–104 | 115–118 | 119–124 | 100–104 |
| (4) Specific rotation $[\alpha]_D^{22}$ C = 0.5% methanol solution | −50.7° | −31.2° | −37.8° | −36.8° | −31.4° |
| (5) Ultraviolet absorption spectrum $E_{1cm}^{1\%}$ | $\lambda_{max}^{MeOH}$ 283 nm 216 | $\lambda_{max}^{MeOH}$ 283 nm 182 | $\lambda_{max}^{MeOH}$ 282 nm 206 | $\lambda_{max}^{MeOH}$ 279 nm 262 | $\lambda_{max}^{MeOH}$ 282 nm 201 |

| analysis | compounds No. 16 | 17 | 18 | 19 | 20 |
|---|---|---|---|---|---|
| (1) Elementary analysis (calculated value) | C:63.00(63.20) H: 8.71( 8.43) N: 1.37( 1.32) | C:61.96(61.58) H: 7.57( 7.84) N: 1.30( 1.28) | C:61.83(61.58) H: 7.59( 7.84) N: 1.22( 1.28) | C:61.20(61.41) H: 7.83( 7.73) N: 1.21( 1.23) | C:61.92(61.41) H: 7.51( 7.73) N: 1.30( 1.23) |
| (2) Molecular weight | 1,064 | 1,092 | 1,092 | 1,134 | 1,134 |
| (3) Melting point (°C.) | 109–114 | 115–118 | 113–116 | 111–114 | 112–114 |
| (4) Specific rotation $[\alpha]_D^{22}$ C = 0.5% methanol solution | −48.0° | −23.0° | −26.4° | −53.8° | −24.2° |
| (5) Ultraviolet absorption spectrum $E_{1cm}^{1\%}$ | $\lambda_{max}^{MeOH}$ 284 nm 191 | $\lambda_{max}^{MeOH}$ 283 nm 186 | $\lambda_{max}^{MeOH}$ 283 nm 173 | $\lambda_{max}^{MeOH}$ 282 nm 191 | $\lambda_{max}^{MeOH}$ 282 nm 191 |

| analysis | compounds No. 21 | 22 | 23 | | |
|---|---|---|---|---|---|
| (1) Elementary analysis (calculated value) | C:59.10(60.44) H: 7.79( 7.52) N: 1.27( 1.17) | C:64.00(64.25) H: 7.50( 7.90) N: 1.50( 1.29) | C:64.28(63.98) H: 7.37( 7.79) N: 1.39( 1.24) | | |
| (2) Molecular weight | 1,192 | 1,084 | 1,126 | | |
| (3) Melting point (°C.) | 95–103 | 118–121 | 110–114 | | |
| (4) Specific rotation $[\alpha]_D^{22}$ C = 0.5% methanol solution | −22.5° | −49.6° | −28.8° | | |
| (5) Ultraviolet absorption spectrum $E_{1cm}^{1\%}$ | $\lambda_{max}^{MeOH}$ 283 nm 156 | $\lambda_{max}^{MeOH}$ 223.5 nm 634 | $\lambda_{max}^{MeOH}$ 282 nm 224 | $\lambda_{max}^{MeOH}$ 223.5 nm 626 | $\lambda_{max}^{MeOH}$ 282 nm 223 |

| analysis | compounds No. 24 | 25 | 26 | 27 | 28 |
|---|---|---|---|---|---|
| (1) Elementary analysis (calculated value) | C:63.57(63.02) H: 8.69( 8.17) N: 1.40( 1.34) | C:62.27(62.79) H: 8.58( 8.04) N: 1.33( 1.28) | C:61.37(61.88) H: 7.80( 7.92) N: 1.30( 1.26) | C:61.65(61.71) H: 7.54( 7.81) N: 1.20( 1.21) | C:60.52(60.73) H: 7.95( 7.60) N: 1.26( 1.16) |
| (2) Molecular weight | 1,048 | 1,090 | 1,106 | 1,148 | 1,206 |
| (3) Melting point (°C.) | 110–112 | 105–109 | 105–111 | 102–106 | 98–102 |
| (4) Specific rotation $[\alpha]_D^{22}$ C = 0.5% methanol solution | −58.6° | −30.2° | −25.2° | −26.2° | −22.0° |
| (5) Ultraviolet absorption spectrum $E_{1cm}^{1\%}$ | $\lambda_{max}^{MeOH}$ 283 nm 210 | $\lambda_{max}^{MeOH}$ 282 nm 205 | $\lambda_{max}^{MeOH}$ 283 nm 172 | $\lambda_{max}^{MeOH}$ 283 nm 176 | $\lambda_{max}^{MeOH}$ 282 nm 150 |

| analysis | compounds No. 29 | 30 | 31 | 32 |
|---|---|---|---|---|
| (1) Elementary analysis (calculated value) | C:62.78(62.66) H: 8.96( 8.70) N: 1.31( 1.33) | C:60.18(60.04) H: 7.62( 7.85) N: 1.39( 1.35) | C:60.75(61.32) H: 8.03( 7.86) N: 2.46( 2.60) | C:61.02(61.46) H: 7.76( 7.82) N: 2.44( 2.47) |
| (2) Molecular weight | 1,054 | 1,040 | 1,077 | 1,133 |
| (3) Melting point (°C.) | 102–106.5 | 115–118 | 109–112 | 96–111 |
| (4) Specific rotation $[\alpha]_D^{22}$ C = 0.5% methanol solution | −46.8° | −32.4° | −28.4° | −25.4° |
| (5) Ultraviolet absorption spectrum $E_{1cm}^{1\%}$ | $\lambda_{max}^{MeOH}$ 283 nm 204 | $\lambda_{max}^{MeOH}$ 237 nm 90 | $\lambda_{max}^{MeOH}$ 283 nm 200 | $\lambda_{max}^{MeOH}$ 283 nm 194 | $\lambda_{max}^{MeOH}$ 283 nm 162 |

Table 3-continued

| analysis | compounds No. | | | | |
|---|---|---|---|---|---|
| | 33 | 34 | 35 | 36 | 37 |
| (1) Elementary analysis (calculated value) | C:59.76(60.03) H: 7.85( 7.93) N: 3.90( 3.88) | C:61.05(60.83) H: 7.95( 7.85) N: 1.38( 1.31) | C:60.87(61.14) H: 8.01( 7.93) N: 1.32( 1.29) | C:61.32(61.14) H: 7.81( 7.93) N: 1.30( 1.29) | C:59.28(58.92) H: 7.44( 7.51) N: 1.25( 1.27) |
| (2) Molecular weight | 1,080 | 1,066 | 1,080 | 1,080 | 1,100 |
| (3) Melting point (°C.) | 110–115 | 105–107 | 104–108 | 103–107 | 108–112 |
| (4) Specific rotation $[\alpha]_D^{22}$ C = 0.5% methanol solution | −29.6° | −49.8° | −48.4° | −40.8° | −46.2° |
| (5) Ultraviolet absorption spectrum $E_{1cm}^{1\%}$ | $\lambda_{max}^{MeOH}$ 283 nm 170 | $\lambda_{max}^{MeOH}$ 283 nm 203 | $\lambda_{max}^{MeOH}$ 283 nm 196 | $\lambda_{max}^{MeOH}$ 283 nm 193 | $\lambda_{max}^{MeOH}$ 281 nm 198 |

| analysis | compounds No. | | | | |
|---|---|---|---|---|---|
| | 38 | 39 | 40 | 41 | 42 |
| (1) Elementary analysis (calculated value) | C:61.28(61.00) H: 7.66( 7.81) N: 1.27( 1.25) | C:61.47(61.15) H: 8.21( 7.93) N: 1.47( 1.30) | C:59.98(60.48) H: 8.70( 8.36) N: 1.27( 1.30) | C:58.86(59.64) H: 8.12( 7.74) N: 2.41( 2.62) | C:58.73(59.55) H: 7.91( 7.63) N: 2.49( 2.53) |
| (2) Molecular weight | 1,122 | 1,080 | 1,072 | 1,067 | 1,109 |
| (3) Melting point (°C.) | 94–98 | 103–107.5 | 112–116 | 116–118 | 108–111 |
| (4) Specific rotation $[\alpha]_D^{22}$ C = 0.5% methanol solution | −19.8° | −40.8° | −37.2° | −54.2° | −35.6° |
| (5) Ultraviolet absorption spectrum $E_{1cm}^{1\%}$ | $\lambda_{max}^{MeOH}$ 283 nm 182 | $\lambda_{max}^{MeOH}$ 284 nm 187 | $\lambda_{max}^{MeOH}$ 283 nm 189 | $\lambda_{max}^{MeOH}$ 273 nm 218 | $\lambda_{max}^{MeOH}$ 273 nm 210 |

| analysis | compounds No. | | | |
|---|---|---|---|---|
| | 43 | 44 | 45 | 46 |
| (1) Elementary analysis (calculated value) | C:58.80(59.05) H: 7.78( 7.61) N: 1.29( 1.27) | C:62.13(61.76) H: 8.46( 7.97) N: 1.30( 1.33) | C:61.60(61.58) H: 7.55( 7.84) N: 1.31( 1.28) | C:62.54(62.07) H: 8.11( 8.05) N: 1.28( 1.32) |
| (2) Molecular weight | 1,098 | 1,050 | 1,092 | 1,064 |
| (3) Melting point (°C.) | 110–116 | 115–117 | 103–107 | 107–112 |
| (4) Specific rotation $[\alpha]_D^{22}$ C = 0.5% methanol solution | −41.0° | −50.6° | −28.6° | −71.6° |
| (5) Ultraviolet absorption spectrum $E_{1cm}^{1\%}$ | $\lambda_{max}^{MeOH}$ 284 nm 177 | $\lambda_{max}^{MeOH}$ 284 nm 204 | $\lambda_{max}^{MeOH}$ 277 nm 192 | $\lambda_{max}^{MeOH}$ 278 nm 205 |

| analysis | compounds No. |
|---|---|
| | 47 |
| (1) Elementary analysis (calculated value) | C:63.85(63.31) H: 7.90( 7.79) N: 1.22( 1.27) |
| (2) Molecular weight | 1,100 |
| (3) Melting point (°C.) | 122–127 |
| (4) Specific rotation $[\alpha]_D^{22}$ C = 0.5% methanol solution | −43.0° |
| (5) Ultraviolet absorption spectrum $E_{1cm}^{1\%}$ | $\lambda_{max}^{MeOH}$ 226 nm 587 $\lambda_{max}^{MeOH}$ 283 nm 197 |

BIOLOGICAL ACTIVITIES (i) Antimicrobial spectrum

Antimicrobial activity of the new antibiotics according to the present invention was measured on various pathogenic microorganisms by the broth dilution mehtod. Tab. 4 shows the minimum inhibitory concentrations (MIC mcg/ml). The new antibiotics show a similar antimicrobial spectrum to that of tylosin as shown in Tab. 4. All the compounds have an excellent antimicrobial activity mainly on gram-positive bacteria. One of the superir properties to the known antibiotics is to show notably higher anitmicrobial activity on various strains that are resistant to the known anitbiotics. Test microorganisms with an asterisk mark (*) in Tab. 4 are all drug-resistant strains that were clinically isolated. More in detail, Staphylococcus aureus MS-8710 is resistant to tylosin, penicillin, tetracycline, erythromycin and leucomycin. Staphylococcus aureus MS-9931 is resistant to tylosin, penicillin, erythromycin, tetracycline, leucomycin, spiramycin and josamycin. And also Streptococcus piogenes is resistant to tylosin, erythromycin, oleandomycin and leucomycin.

Table 4

| No. | compounds | | Staphylococcus aureus FDA-209P | Staphylococcus aureus SMITH | Bacillus cereus ATCC 9634 | Sarcina lutea ATCC 9341 | Staphylococcus aureus MS-8710 | Staphylococcus aureus MS-9937 | Staphylococcus aureus MS-9931 | Streptococcus pyogenes MH-771 |
|---|---|---|---|---|---|---|---|---|---|---|
| | tylosin (control) | | 0.39 | 0.39 | 0.78 | 0.19 | >200 | 100 | 200 | >200 |
| | 3-acetyltylosin (control) | | 0.39 | 0.39 | 0.78 | 0.19 | >200 | 100 | 200 | 200 |
| | 2'-acetyltylosin | reference | 1.56 | 1.56 | 1.56 | 0.39 | >200 | 200 | 200 | >200 |
| | 2'-propionyltylosin | | 1.56 | 1.56 | 1.56 | 0.39 | >200 | 200 | 200 | >200 |
| | 2'-monochloroacetyltylosin | | 1.56 | 1.56 | 1.56 | 0.39 | >200 | 200 | 200 | >200 |
| | 3,2'-diacetyltylosin | | 1.56 | 1.56 | 1.56 | 0.39 | >200 | 200 | 200 | >200 |
| 1 | 2'-acetyl-4'''-monochloroacetyltylosin | | 1.56 | 1.56 | 1.56 | 0.78 | >200 | 200 | 200 | 200 |
| 2 | 2'-acetyl-4'''-trichloroacetyltylosin | | 1.56 | 1.56 | 1.56 | 0.39 | 200 | 100 | 100 | 100 |
| 3 | 3,2'-diacetyl-4'''-monochloroacetyltylosin | | 1.56 | 1.56 | 1.56 | 0.78 | 100 | 100 | 100 | 100 |
| 4 | 3,2'-diacetyl-4'''-trichloroacetyltylosin | | 1.56 | 1.56 | 1.56 | 0.39 | 100 | 100 | 100 | 100 |
| 5 | 2'-acetyl-4'''-phenoxyacetyltylosin | | 0.78 | 0.78 | 0.78 | 0.39 | 100 | 100 | 100 | 100 |
| 6 | 3,2'-diacetyl-4'''-carboethoxytylosin | | 0.78 | 0.78 | 0.78 | 0.39 | 100 | 100 | 100 | 100 |
| 7 | 4''-n-caproyltylosin | | 0.78 | 0.78 | 0.78 | 0.39 | 12.5 | 12.5 | 25 | 6.25 |
| 8 | 3-acetyl-4''-n-caproyltylosin | | 0.39 | 0.78 | 0.78 | 0.39 | 25 | 25 | 25 | 6.25 |
| 9 | 4''-n-capryltylosin | | 0.78 | 0.78 | 1.56 | 0.39 | 25 | 25 | 25 | 25 |
| 10 | 4''-n-caproyltylosin | | 1.56 | 1.56 | 1.56 | 0.78 | 100 | 100 | 50 | 50 |
| 11 | 4''-iso-caproyltylosin | | 0.78 | 0.78 | 0.78 | 0.39 | 12.5 | 12.5 | 12.5 | 6.25 |
| 12 | 4''-α-methyl-n-valeryltylosin | | 1.56 | 1.56 | 0.78 | 0.39 | 25 | 25 | 100 | 6.25 |
| 13 | 3-acetyl-4''-α-ethyl-n-butyryltylosin | | 0.39 | 0.78 | 0.78 | 0.19 | 25 | 25 | 25 | 12.5 |
| 14 | 4''-(4-nitrophenyl)acetyltylosin | | 0.39 | 0.39 | 0.39 | 0.19 | 6.25 | 6.25 | 6.25 | 3.13 |
| 15 | 3-acetyl-4''-α-phenylpropionyltylosin | | 0.39 | 0.39 | 0.78 | 0.19 | 25 | 25 | 25 | 12.5 |
| 16 | 4''-α-phenyl-n-butyryltylosin | | 0.39 | 0.39 | 0.78 | 0.19 | 12.5 | 12.5 | 25 | 6.25 |
| 17 | 3-acetyl-4''-D-(α-hydroxyphenylacetyl)tylosin | | 12.5 | 12.5 | 6.25 | | 25 | | | |
| 18 | 3-acetyl-4''-L-(α-hydroxyphenylacetyl)tylosin | | 0.78 | 0.78 | 0.78 | 0.39 | 25 | 12.5 | 12.5 | 6.25 |
| 19 | 3-acetyl-4''-D-(α-acetoxyphenylacetyl)tylosin | | 1.56 | 0.78 | 0.78 | 0.78 | 100 | 100 | 100 | 25 |
| 20 | 3-acetyl-4''-L-(α-acetoxyphenylacetyl)tylosin | | 0.78 | 1.56 | 1.56 | 0.39 | 50 | 100 | 100 | 12.5 |
| 21 | 3-acetyl-4''-[α-acetoxy-(4-acetoxyphenyl)acetyl]tylosin | | 0.78 | 0.78 | 0.78 | 0.39 | 50 | 50 | 50 | 12.5 |
| 22 | 4''-α-naphthylacetyltylosin | | 1.56 | 1.56 | 1.56 | 0.39 | 12.5 | 25 | 25 | 50 |
| 23 | 3-acetyl-4''-α-naphthyylacetyltylosin | | 0.78 | 0.78 | 0.78 | 0.39 | 25 | 50 | 25 | 25 |
| 24 | 4''-β-phenylpropionyltylosin | | 0.78 | 0.39 | 0.78 | 0.19 | 12.5 | 25 | 12.5 | 25 |
| 25 | 3-acetyl-4''-β-phenylpropionyltylosin | | 1.56 | 0.78 | 0.78 | 0.39 | 50 | 50 | 50 | 25 |
| 26 | 3-acetyl-4''-L-[(α-hydroxy-β- | | | | | | | | | |

Table 4-continued

| | | | | MIC (mcg/ml) | | | | |
|---|---|---|---|---|---|---|---|---|
| No. | compounds | Staphylococcus aureus FDA-209P | Staphylococcus aureus SMITH | Bacillus cereus ATCC 9634 | Sarcina lutea ATCC 9341 | Staphylococcus* aureus MS-8710 | Staphylococcus* aureus MS-9937 | Staphylococcus* aureus MS-9931 | Streptococcus* pyogenes MH-771 |
| 27 | 3-acetyl-4''-L-[(α-acetoxy-β-phenyl)propionyl]tylosin | 0.78 | 0.78 | 0.78 | 0.39 | 50 | 50 | 50 | 12.5 |
| 28 | 3-acetyl-4''-[α-acetoxy-β-(4-acetoxyphenyl)propionyl]tylosin | 0.78 | 0.78 | 0.78 | 0.39 | 50 | 50 | 50 | 25 |
| 29 | 4''-β-cyclohexylpropionyltylosin | 1.56 | 1.56 | 1.56 | 0.78 | 25 | 25 | 25 | 25 |
| 30 | 4''-thienylacetyltylosin | 0.78 | 0.78 | 0.78 | 0.39 | 12.5 | 12.5 | 12.5 | 6.25 |
| 31 | 3-acetyl-4''-(3-pyridyl)acetyl-tylosin | 0.39 | 0.39 | 0.39 | 0.19 | 12.5 | 25 | 25 | 6.25 |
| 32 | 3-acetyl-4''-(N-acetylanilino)acetyltylosin | 0.39 | 0.39 | 0.39 | 0.19 | 12.5 | 12.5 | 12.5 | 6.25 |
| 33 | 3-acetyl-4''-(1-imidazolyl)propionyltylosin | 0.78 | 0.78 | 0.78 | 0.39 | 12.5 | 25 | 25 | 12.5 |
| 34 | 4''-phenylthioacetyltylosin | 1.56 | 1.56 | 1.56 | 0.78 | 25 | 50 | 50 | 12.5 |
| 35 | 4''-(4-methylphenyl)thioacetyl-tylosin | 0.39 | 0.39 | 0.39 | 0.19 | 6.25 | 12.5 | 12.5 | 6.25 |
| 36 | 4''-(3-methylphenyl)thioacetyl tylosin | 1.56 | 1.56 | 1.56 | 0.78 | 25 | 50 | 25 | 12.5 |
| 37 | 4''-(4-chlorophenyl)thioacetyl-tylosin | 0.78 | 0.78 | 0.78 | 0.39 | 25 | 50 | 50 | 25 |
| 38 | 3-acetyl-4''-benzylthioacetyl-tylosin | 0.39 | 0.39 | 0.78 | 0.19 | 12.5 | 6.25 | 6.25 | 3.13 |
| 39 | 4''-β-phenylthiopropionyltylosin | 0.78 | 0.78 | 1.56 | 0.39 | 12.5 | 12.5 | 12.5 | 6.25 |
| 40 | 4''-cyclohexylthioacetyltylosin | 0.78 | 0.39 | 0.39 | 0.19 | 12.5 | 12.5 | 12.5 | 6.25 |
| 41 | 4''-(4-pyridyl)thioacetyltylosin | 0.78 | 0.78 | 0.78 | 0.39 | 12.5 | 25 | 25 | 6.25 |
| 42 | 3-acetyl-4''-(4-pyridyl)thioacetyl-tylosin | 0.78 | 0.39 | 0.39 | 0.19 | 12.5 | 12.5 | 12.5 | 12.5 |
| 43 | 4''-benzenesulfonylacetyltylosin | 0.39 | 0.39 | 0.39 | 0.19 | 6.25 | 6.25 | 12.5 | 3.13 |
| 44 | 4''-phenoxyacetyltylosin | 0.78 | 0.78 | 0.78 | 0.39 | 6.25 | 6.25 | 6.25 | 3.13 |
| 45 | 3-acetyl-4''-phenoxyaetylthiosin | 0.39 | 0.39 | 0.39 | 0.19 | 25 | 25 | 25 | 6.25 |
| 46 | 4''-α-phenoxypropionyltylosin | 0.39 | 0.39 | 0.39 | 0.19 | 100 | 25 | 25 | 12.5 |
| | 4''-β-naphthoxyacetyltylosin | 0.78 | 0.39 | 0.39 | 0.19 | 25 | 50 | 25 | 12.5 |
| 47 | | 0.78 | 0.78 | 0.78 | 0.19 | 25 | 25 | 25 | 12.5 |

Furthermore the new antibiotics according to the present invention also show antimicrobial activity on Mycoplasma. In particular, it is noteworthy that they have much higher antimicrobial activity than tylosin on Mycoplasma that is resistant to macrolide antibiotics. Tab. 5 shows the antimicrobial activity on various strains of Mycoplasma gallisepticum of 3-acetyl-4''-D-(α-hydroxyphenylacetyl)tylosin, 4''-β-phenylpropionyltylosin, 4''-β-cyclohexylpropionyltylosin, 3-acetyl-4''-(N-acetylanilino)-acetyltylosin, 4''-phenylthioacetyltylosin, 3-acetyl-4''-benzylthioacetyltylosin, 4''-cyclohexylthioacetyltylosin, 4''-(4-pyridyl)thioacetyltylosin, and 4''-benzenesulfonylacetyltylosin.

Table 5

Antibactrial activity against Mycoplasma

| Strain | MIC (mcg/ml)** | | | |
|---|---|---|---|---|
| | Mycoplasma gallisepticum | | | |
| No. compounds | KP-13 | E-5* | E-11* | A-72* |
| 17 3-acetyl-4''-D-(α-hydroxyphenyl-acetyl)tylosin | 0.157 | 0.625 | 0.625 | 0.313 |
| 24 4''-β-phenylpropionyltylosin | 0.078 | 0.313 | 0.313 | 0.157 |
| 29 4''-β-4''-β-cyclohexylpropionyltylosin | 0.039 | 0.313 | 0.625 | 0.313 |
| 32 3-acetyl-4''-(N-acetylanilino)acetyltylosin | 0.157 | 0.313 | 0.313 | 0.157 |
| 34 4''-phenylthioacetyltylosin | 0.019 | 0.078 | 0.078 | 0.078 |
| 38 3-acetyl-4''-benzylthioacetyltylosin | 0.019 | 0.078 | 0.078 | 0.078 |
| 40 4''-cyclohexylthioacetyltylosin | 0.078 | 0.157 | 0.157 | 0.157 |
| 41 4''-(4-pyridyl)thioacetyltylosin | 0.039 | 0.313 | 0.313 | 0.157 |
| 43 4''-benzenesulfonylacetyltylosin | 0.019 | 0.078 | 0.078 | 0.039 |
| tylosin (control) | 0.019 | 2.50 | 2.50 | 2.50 |

Note
*Macrolide resistant strain
**Medium (Eiken PPLO Medium)

(ii) Blood level

The new antibiotics according to the present invention were each orally administered to mice at a dose of 100 mg/kg. Each blood level was then measured and compared with those of tylosin and 3-acetyltylosin.

The highest blood level of tylosin was 1 mcg/ml and less when measured by the bioassay with Sarcina lutea. In the case of 3-acetyltylosin the highest was 2–5 mcg/ml. On the other hand, all the 4''-acyl derivatives according to the present invention showed higher blood levels such as 5–20 mcg/ml 1–1.5 hours after administration. For example 3-acetyl-4''-D-(α-hydroxyphenylacetyl)tylosin showed a blood level of 10 mcg/ml after 1 hour of the oral administration at 100 mg/kg and 2 mcg/ml after 3 hours.

4''-Phenylpropionyltylosin, when given orally at a dose of 100 mg/kg, showed a blood level of 12 mcg/ml after 1 hour of administration and 2 mcg/ml after 3 hours, respectively. It was clearly demonstrated that the compounds according to the present invention showed higher absorbability than tylosin and 3-acetyltylosin.

(iii) Toxicity

The toxicity of all compounds shown by the $LD_{50}$ value of the new antibiotics according to the present invention were 500 mg/kg and more when administered to mice intraperitoneally. When given orally all the $LD_{50}$ values were 2000 mg/kg and more, respectively.

3-Acetyl-4''-D-(α-hydroxyphenylacetyl)tylosin, 4''-phenylthioacetyltylosin and 4''-benzenesulfonylacetyltylosin, selected as the representative compounds according to the present invention, were mixed with feed at a ratio of 0.3%, respectively and given to chickens for a month. No toxicity was observed.

Accordingly, there are provided by the present invention new antibiotics that show an excellent antimicrobial activity on various pathogenic microorganisms and drug-resistant strains thereof and also showed a much higher blood level in mice than tylosin and 3-acetyltylosin when given orally. In addition they have low toxicity. Therefore these compounds are medically superior antibiotic derivatives and useful as a therapeutic agent particularly on infections by gram-positive bacteria. And also they have higher therapeutic and preservative effect than tylosin on respiratory Mycoplasma infection (CRD) and mixed infection with pathogenic microorganisms such as Staphylococcus aureus (CCRD) in animals. Accordingly the new antibiotics are useful compounds as feed-additives.

The following examples further illustrate in detail the process for producing the tylosin derivatives according to the present invention.

EXAMPLE 1

4''-β-Phenylpropionyltylosin (Compound No.24)

2'-Acetyl-4'''-monochloroacetyltylosin (200 mg) was dissolved in 2 ml of methylene chloride. To the solution was added 0.47 ml of pyridine. The solution was cooled at −10° C. and 0.1 ml of β-phenylpropionyl chloride was added. After 30 minutes at −10°−−5° C., 100 ml of benzene was poured in the mixture to terminate the reaction. The benzene layer was washed with saturated aqueous solution of sodium bicarbonate, sodium acetate-sulfuric acid buffer solution (pH 5.0) and saturated sodium chloride solution successively, and dried and concentrated by evaporation under reduced pressure. The resulting residue was subjected to chromatography on a silica gel column (Wako Pure Chemicals, C-200, 1.7 cm in outer diameter and 15 cm in length). Concentration of the eluate with benzene-acetone (10–15% V/V acetone) provided 85 mg of 2'-acetyl-4'''-monochloroacetyl-4''-β-phenylpropionyltylosin in white powder. The white powder was dissolved in 10 ml of methanol and refluxed for 22 hours. Crude 4''-β-phenylpropionyltylosin was obtained by evaporation of methanol. The crude preparation was subjected to chromatography on a silica gel column. Elution was carried out with benzene-acetone (20% V/V acetone). Fractions containing the aimed product were combined and concentrated to give 87 mg of 4''-β-phenylpropionyltylosin (m.p. 110°–112° C., $[\alpha]_D^{22} = -58.6°$ (C=0.5 MeOH), $\lambda_{max}^{MeOH} = 283$ nm and $E_{1\ cm}^{1\%} = 210$).

EXAMPLE 2

3-Acetyl-4''-D-(α-hydroxyphenylacetyl)tylosin (Compound No.17)

3,2'-Diacetyl-4'''-trichloroacetyltylosin (250 mg) was dissolved in 4.5 ml of methylene chloride. To the solution was added 103 mg of pyridine. The solution was cooled at −5° C. and 215 mg of D-α-monochloroacetoxyphenylacetyl chloride was added. After 1.5 hours at the same temperature, the reaction mixture was poured into 100 ml of benzene. The benzene layer was washed with saturated aqueous solutions of sodium bicarbonate and of sodium chloride successively, and then dried with anhydrous sodium sulfate and concentrated by evaporation under reduced pressure. The resulting crude product was purified by silica gel chromatography to give 184 mg of 3,2'-diacetyl-4'''-trichloroacetyl-4"-D-(α-monochloroacetoxy-phenylacetyl)tylosin in white powder. The white powder was dissolved in 10 ml of methanol and refluxed for 18 hours. The methanol was evaporated out under reduced pressure. Purification of the resulted residue by chromatography on silica gel gave 112 mg of the aimed 3-acetyl-4"-D-(α-hydroxyphenylacetyl)tylosin in white powder (m.p. 115°–118° C., $[\alpha]_D^{22} = -23.0°$ (C=0.5 MeOH), $\lambda_{max.}^{MeOH} = 283$ nm and $E_{1\ cm}^{1\%} = 186$).

EXAMPLE 3

4"-Benzenesulfonylacetyltylosin (Compound No.43)

2'-Acetyl-4"'-trichloroacetyltylosin (250 mg) was dissolved in 6 ml of methylene chloride. To the solution was added 108 mg of pyridine. The solution was cooled at −5° C. and 198 mg of benzenesulfonylacetyl chloride was added. After 10 minutes at the same temperature, the reaction mixture was treated in the same manner as described in Example 1. The obtained white powder (152 mg) of 2'-acetyl-4"'-trichloroacetyl-4"-benzenesulfonylacetyltylosin was dissolved in 10 ml of methanol and refluxed for 22 hours. The aimed 4"-benzenesulfonylacetyltylosin was obtained by evaporating the methanol under reduced pressure. Further purification by chromatography on silica gel provided 66 mg of 4"-benzenesulfonylacetyltylosin in white powder (m.p. 110°–116° C., $[\alpha]_D^{22} = -41.0°$ (C=0.5 MeOH), $\lambda_{max.}^{MeOH} = 284$ nm and $E_{1\ cm}^{1\%} = 177$).

Figure 1:
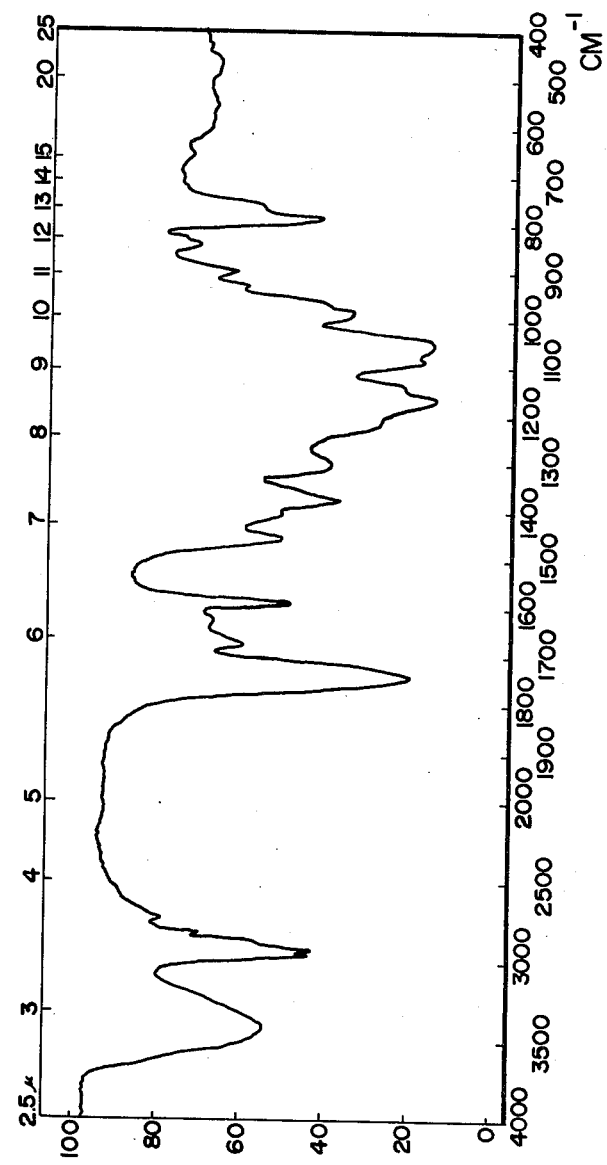
FIG. 1 shows the infrared absorption spectrum (KBr tablet) of 2'-acetyl-4"'-monochloroacetyltylosin (Compound No.1) according to the present invention.
Figure 2:
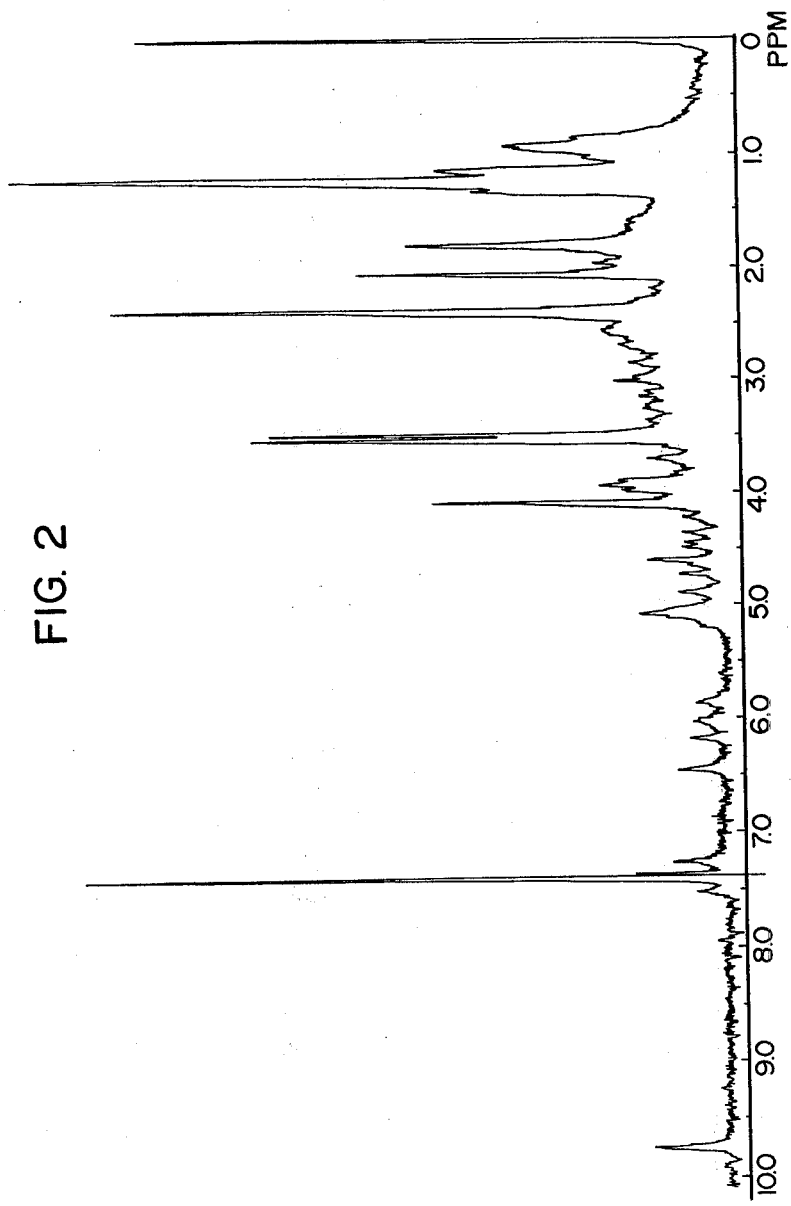
FIG. 2 shows the nuclear magnetic resonance spectrum (60 MHz, heavy chloroform) of Compound No. 1.
Figure 3:
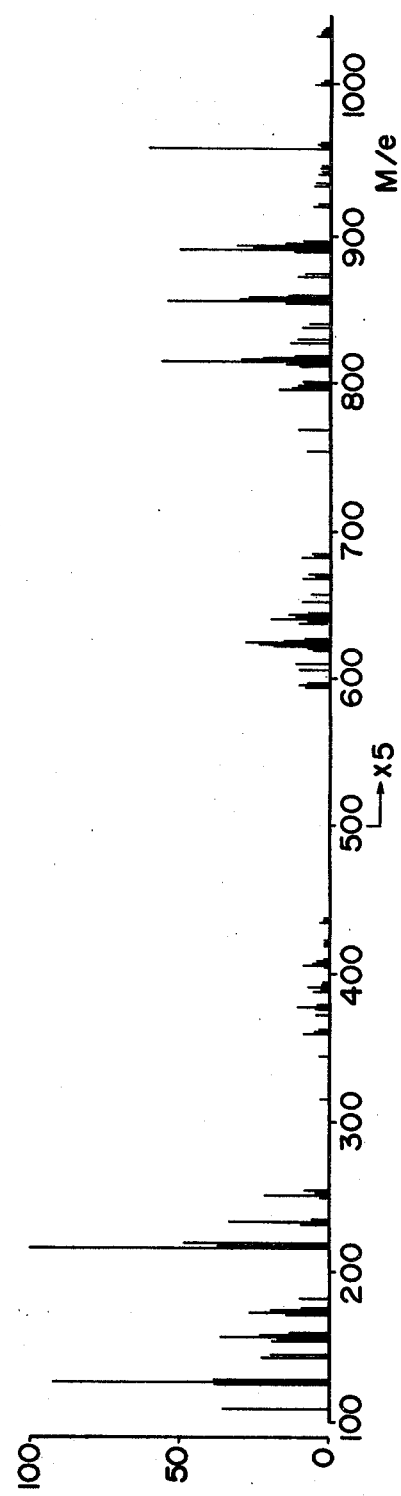
FIG. 3 shows chemical ionization-type mass spectrum (CI-MS) of Compound No.1.
Figure 4:
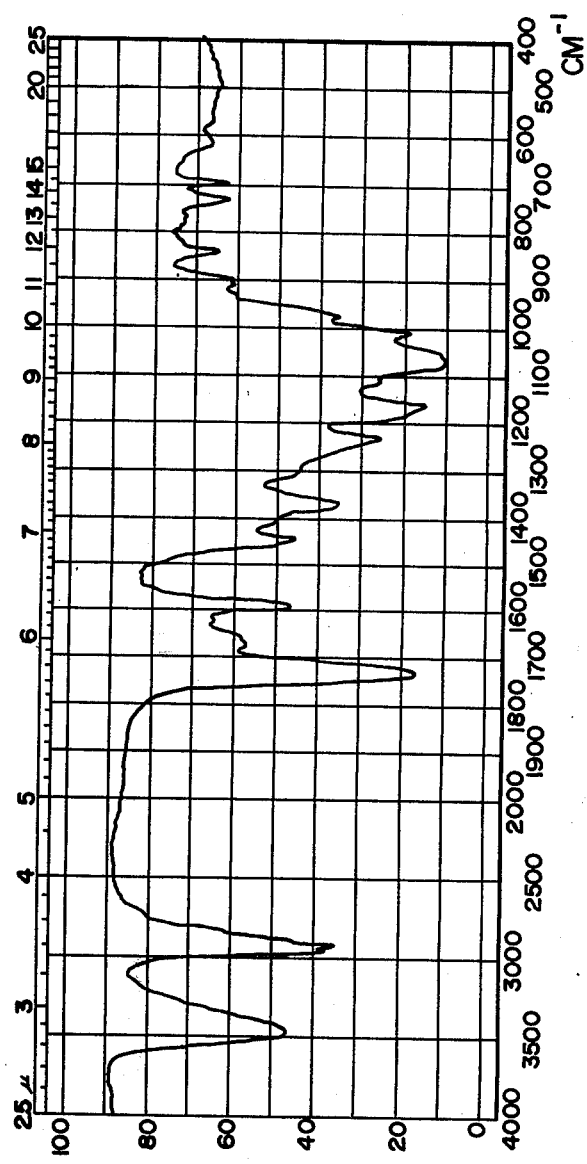
FIG. 4 shows the infrared absorption spectrum (KBr tablet) of 3-acetyl-4"-D-(α-hydroxyphenylacetyl)-tylosin (Compound No.17) according to the present invention.
Figure 5:
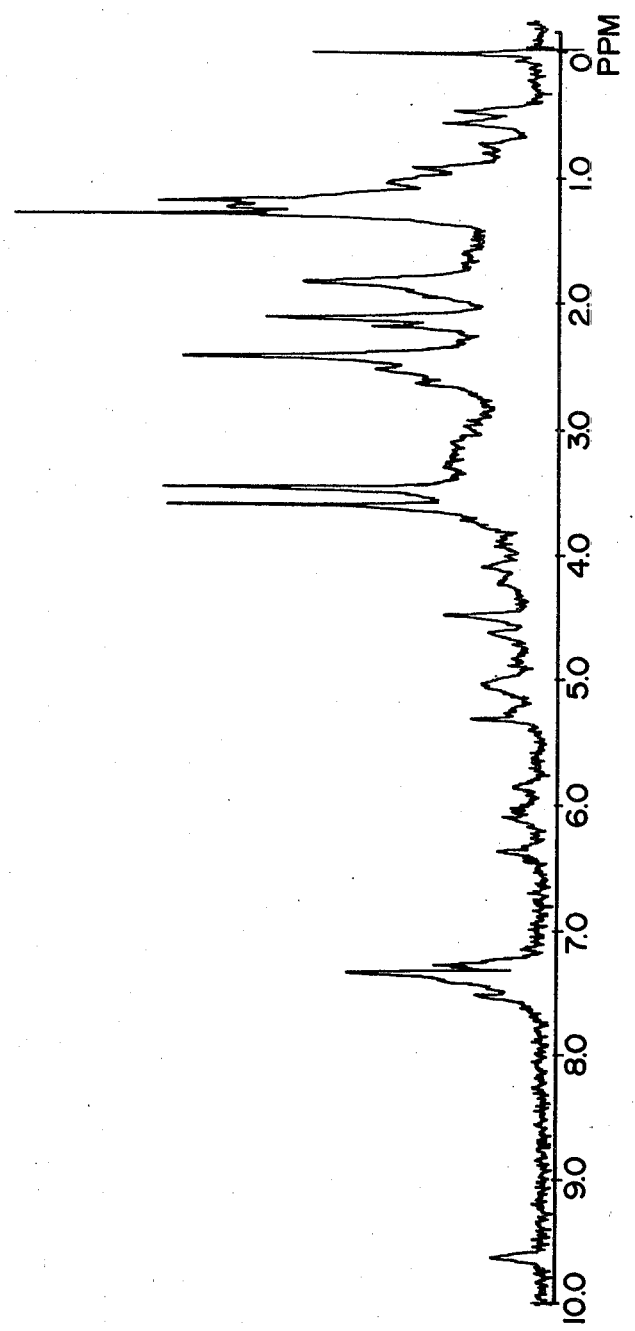
FIG. 5 shows the nuclear magnetic resonance spectrum (60 MHz, heavy chloroform) of Compound No.17.

What is claimed:

1. An acyl derivative of tylosin of the following formula I:

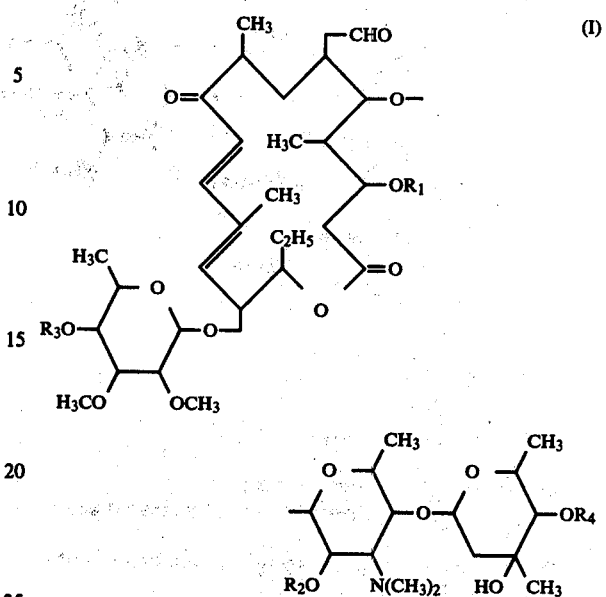

wherein $R_1$ represents hydrogen or acetyl, $R_2$ represents hydrogen, acetyl, propionyl or chlorinated acetyl, $R_3$ represents hydrogen, chlorinated acetyl, carboethoxy or phenoxyacetyl, and $R_4$ represents hydrogen or

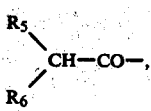

wherein $R_5$ represents hydrogen, methyl, ethyl, hydroxyl or acetoxy, and $R_6$ represents an alkyl having 3 to 8 carbons (when the number of the carbons is 3, $R_5$ being a group other than hydrogen), phenyl, 4-nitrophenyl, 4-acetoxyphenyl, naphthyl, benzyl, 4-acetoxybenzyl, cyclohexylmethyl, thienyl, pyridyl, N-acetylanilino, imidazolylmethyl, phenylthio, 4-methylphenylthio, 3-methylphenylthio, 4-chlorophenylthio, benzylthio, phenylthiomethyl, cyclohexylthio, pyridylthio, benzenesulfonyl, phenoxy, naphthoxy or phenoxymethyl, with the proviso that when $R_4$ represents hydrogen, $R_2$ and $R_3$ each represents a group other than hydrogen, and when $R_4$ represents a group other than hydrogen, $R_2$ and $R_3$ each represents hydrogen and a nontoxic acid addition salt thereof.

2. An acyl derivative of tylosin according to claim 1 having the following formula II:

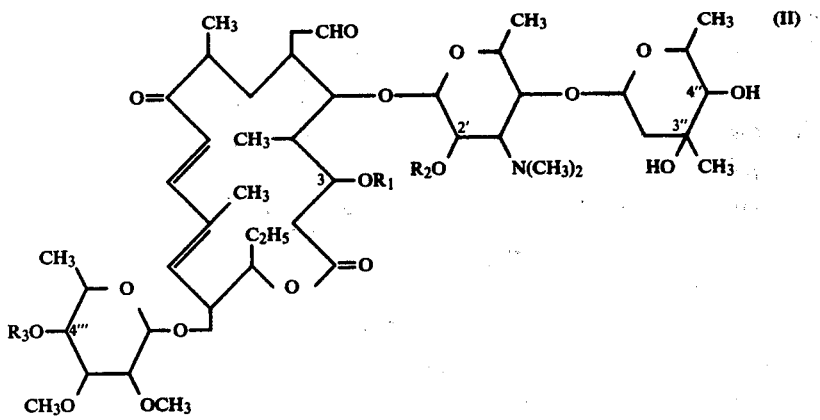

wherein
 $R_1$ represents hydrogen or acetyl,
 $R_2$ represents acetyl, propionyl or chlorinated acetyl, and
 $R_3$ represents chlorinated acetyl, carboethoxy or phenoxyacetyl and
a nontoxic acid addition salt thereof.

3. An acyl derivative according to claim 1 or 2 wherein the derivative is 2'-acetyl-4'''-monochloroacetyltylosin and a nontoxic acid addition salt thereof.

4. An acyl derivative according to claim 1 or 2 wherein the derivative is 2'-acetyl-4'''-trichloroacetyltylosin and a nontoxic acid addition salt thereof.

5. An acyl derivative according to claim 1 or 2 wherein the derivative is 3,2'-diacetyl-4'''-monochloroacetyltylosin and a nontoxic acid addition salt thereof.

6. An acyl derivative according to claim 1 or 2 wherein the derivative is 3,2'-diacetyl-4'''-trichloroacetyltylosin and a nontoxic acid addition salt thereof.

7. An acyl derivative according to claim 1 or 2 wherein the derivative is 2'-acetyl-4'''-phenoxyacetyltylosin and a nontoxic acid addition salt thereof.

8. An acyl derivative according to claim 1 or 2 wherein the derivative is 3,2'-diacetyl-4'''-carboethoxytylosin and a nontoxic acid addition salt thereof.

9. An acyl derivative of tylosin according to claim 1 having the following formula IV:

$R_2$ represents hydrogen,
 $R_3$ represents hydrogen,
 $R_5$ represents hydrogen, methyl, ethyl, hydroxyl or acetoxy, and
 $R_6$ represents an alkyl having 3 to 8 carbons (when the number of the carbons is 3, $R_5$ being a group other than hydrogen), phenyl, 4-nitrophenyl, 4-acetoxyphenyl, naphthyl, benzyl, 4-acetoxybenzyl, cyclohexylmethyl, thienyl, pyridyl, N-acetylanilino, imidazolylmethyl, phenylthio, 4-methylphenylthio, 3-methylphenylthio, 4-chlorophenylthio, benzylthio, phenylthiomethyl, cyclohexylthio, pyridylthio, benzenesulfonyl, phenoxy, naphthoxy or phenoxymethyl, and
a nontoxic acid addition salt thereof.

10. An acyl derivative according to claim 1 or 9 wherein the derivative is 4''-n-caproyltylosin and a nontoxic acid addition salt thereof.

11. An acyl derivative according to claim 1 or 9 wherein the derivative is 3-acetyl-4''-n-caproyltylosin and a nontoxic acid addition salt thereof.

12. An acyl derivative according to claim 1 or 9 wherein the derivative is 4''-n-caprylyltylosin and a nontoxic acid addition salt thereof.

13. An acyl derivative according to claim 1 or 9 wherein the derivative is 4''-n-capryltylosin and a nontoxic acid addition salt thereof.

14. An acyl derivative according to claim 1 or 9 wherein the derivative is 4''-iso-caproyltylosin and a nontoxic acid addition salt thereof.

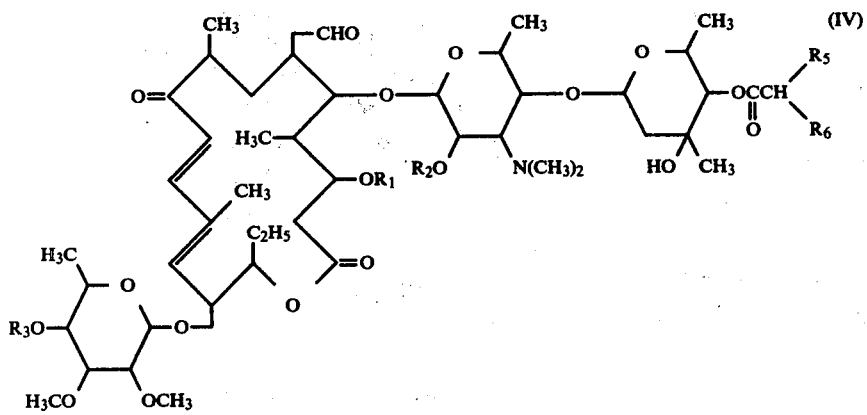

wherein
 $R_1$ represents hydrogen or acetyl,

15. An acyl derivative according to claim 1 or 9 wherein the derivative is 4"-methyl-n-valeryltylosin and a nontoxic acid addition salt thereof.

16. An acyl derivative according to claim 1 or 9 wherein the derivative is 3-acetyl-4"-ethyl-n-butyryltylosin and a nontoxic acid addition salt thereof.

17. An acyl derivative according to claim 1 or 9 wherein the derivative is 4"-(4-nitrophenyl)acetyltylosin and a nontoxic acid addition salt thereof.

18. An acyl derivative according to claim 1 or 9 wherein the derivative is 3-acetyl-4"-α-phenylpropionyltylosin and a nontoxic acid addition salt thereof.

19. An acyl derivative according to claim 1 or 9 wherein the derivative is 4"-α-phenyl-n-butyryltylosin and a nontoxic acid addition salt thereof.

20. An acyl derivative according to claim 1 or 9 wherein the derivative is 3-acetyl-4"-D-(α-hydroxyphenylacetyl)tylosin and a nontoxic acid addition salt thereof.

21. An acyl derivative according to claim 1 or 9 wherein the derivative is 3-acetyl-4"-L-(α-hydroxyphenylacetyl)tylosin and a nontoxic acid addition salt thereof.

22. An acyl derivative according to claim 1 or 9 wherein the derivative is 3-acetyl-4"-D-(α-acetoxyphenylacetyl)tylosin and a nontoxic acid addition salt thereof.

23. An acyl derivative according to claim 1 or 9 wherein the derivative is 3-acetyl-4"-L-(α-acetoxyphenylacetyl)tylosin and a nontoxic acid addition salt thereof.

24. An acyl derivative according to claim 1 or 9 wherein the derivative is 3-acetyl-4"-[α-acetoxy-(4-acetoxyphenyl)acetyl] tylosin and a nontoxic acid addition salt thereof.

25. An acyl derivative according to claim 1 or 9 wherein the derivative is 4"-α-naphthylacetyltylosin and a nontoxic acid addition salt thereof.

26. An acyl derivative according to claim 1 or 9 wherein the derivative is 3-acetyl-4"-α-naphthylacetyltylosin and a nontoxic acid addition salt thereof.

27. An acyl derivative according to claim 1 or 9 wherein the derivative is 4"-β-phenylpropionyltylosin and a nontoxic acid addition salt thereof.

28. An acyl derivative according to claim 1 or 9 wherein the derivative is 3-acetyl-4"-β-phenylpropionyltylosin and a nontoxic acid addition salt thereof.

29. An acyl derivative according to claim 1 or 9 wherein the derivative is 3-acetyl-4"-L-[(α-hydroxy-β-phenyl)propionyl]tylosin and a nontoxic acid addition salt thereof.

30. An acyl derivative according to claim 1 or 9 wherein the derivative is 3-acetyl-4"-L-[(α-acetoxy-β-phenyl)propionyl] tylosin and a nontoxic acid addition salt thereof.

31. An acyl derivative according to claim 1 or 9 wherein the derivative is 3-acetyl-4"-[α-acetoxy-β-(4-acetoxyphenyl)propionyl] tylosin and a nontoxic acid addition salt thereof.

32. An acyl derivative according to claim 1 or 9 wherein the derivative is 4"-β-cyclohexylpropionyltylosin and a nontoxic acid addition salt thereof.

33. An acyl derivative according to claim 1 or 9 wherein the derivative is 4"-thienylacetyltylosin and a nontoxic acid addition salt thereof.

34. An acyl derivative according to claim 1 or 9 wherein the derivative is 3-acetyl-4"-(3-pyridyl)acetyltylosin and a nontoxic acid addition salt thereof.

35. An acyl derivative according to claim 1 or 9 wherein the derivative is 3-acetyl-4"-(N-acetylanilino)acetyltylosin and a nontoxic acid addition salt thereof.

36. An acyl derivative according to claim 1 or 9 wherein the derivative is 3-acetyl-4"-(1-imidazolyl)propionyltylosin and a nontoxic acid addition salt thereof.

37. An acyl derivative according to claim 1 or 9 wherein the derivative is 4"-phenylthioacetyltylosin and a nontoxic acid addition salt thereof.

38. An acyl derivative according to claim 1 or 9 wherein the derivative is 4"-(4-methylphenyl)thioacetyltylosin and a nontoxic acid addition salt thereof.

39. An acyl derivative according to claim 1 or 9 wherein the derivative is 4"-(3-methylphenyl)thioacetyltylosin and a nontoxic acid addition salt thereof.

40. An acyl derivative according to claim 1 or 9 wherein the derivative is 4"-(4-chlorophenyl)thioacetyltylosin and a nontoxic acid addition salt thereof.

41. An acyl derivative according to claim 1 or 9 wherein the derivative is 3-acetyl-4"-benzylthioacetyltylosin and a nontoxic acid addition salt thereof.

42. An acyl derivative according to claim 1 or 9 wherein the derivative is 4"-β-phenylthiopropionyltylosin and a nontoxic acid addition salt thereof.

43. An acyl derivative according to claim 1 or 9 wherein the derivative is 4"-cyclohexylthioacetyltylosin and a nontoxic acid addition salt thereof.

44. An acyl derivative according to claim 1 or 9 wherein the derivative is 4"-(4-pyridyl)thioacetyltylosin and a nontoxic acid addition salt thereof.

45. An acyl derivative according to claim 1 or 9 wherein the derivative is 3-acetyl-4"-(4-pyridyl)thioacetyltylosin and a nontoxic acid addition salt thereof.

46. An acyl derivative according to claim 1 or 9 wherein the derivative is 4"-benzenesulfonylacetyltylosin and a nontoxic acid addition salt thereof.

47. An acyl derivative according to claim 1 or 9 wherein the derivative is 4"-phenoxyacetyltylosin and a nontoxic acid addition salt thereof.

48. An acyl derivative according to claim 1 or 9 wherein the derivative is 3-acetyl-4"-phenoxyacetyltylosin and a nontoxic acid addition salt thereof.

49. An acyl derivative according to claim 1 or 9 wherein the derivative is 4"-α-phenoxypropionyltylosin and a nontoxic acid addition salt thereof.

50. An acyl derivative according to claim 1 or 9 wherein the derivative is 4"-β-naphthoxyacetyltylosin and a nontoxic acid addition salt thereof.

* * * * *